(12) United States Patent
Renner

(10) Patent No.: US 6,853,702 B2
(45) Date of Patent: Feb. 8, 2005

(54) RADIATION THERAPY DOSIMETRY QUALITY CONTROL PROCESS

(76) Inventor: Wendel Dean Renner, 5975 Gales La., Columbia, MD (US) 21045

( * ) Notice: Subject to any disclaimer, the term of this patent is extended or adjusted under 35 U.S.C. 154(b) by 335 days.

(21) Appl. No.: 09/736,351

(22) Filed: Dec. 15, 2000

(65) Prior Publication Data

US 2003/0076926 A1 Apr. 24, 2003

(51) Int. Cl.[7] ................................................ A61N 5/10
(52) U.S. Cl. ............................................ 378/65; 378/64
(58) Field of Search ............................. 378/65, 8, 11, 378/12, 16, 18, 19, 95, 147, 165, 210

(56) References Cited

U.S. PATENT DOCUMENTS

| | | | | |
|---|---|---|---|---|
| 5,394,452 A | * | 2/1995 | Swerdloff et al. | 378/65 |
| 5,754,622 A | * | 5/1998 | Hughes | 378/65 |
| 6,038,283 A | * | 3/2000 | Carol et al. | 378/65 |
| 6,038,284 A | * | 3/2000 | Hernandez-Guerra et al. | 378/65 |
| 6,175,761 B1 | * | 1/2001 | Frandsen et al. | 600/436 |
| 6,438,202 B1 | * | 8/2002 | Olivera et al. | 378/65 |

* cited by examiner

*Primary Examiner*—David V Bruce

(57) ABSTRACT

A treatment verification process for radiation therapy consisting of measuring each of the radiation beams that are to be applied to the patient by making a calibrated image of the field for each beam. The measured beams are then processed and converted to relative monitor units. Software like a treatment planning system is then used to compute the dose to the patient for comparison with the intended treatment prescription.

4 Claims, 3 Drawing Sheets

RADIATION THERAPY DOSIMETRY QUALITY CONTROL PROCESS

BACKGROUND OF THE INVENTION

1. Technical Field

This invention concerns a process for verification of the radiation dose delivered to patients undergoing radiation therapy.

2. Prior Art

Medical linear accelerators and Cobalt 60 external beam units {represented by 22 in FIGS. 1 and 2) are well known machines used to treat human beings for cancer. The radiation source in these machines are generally mounted in a gantry that can rotate around the patient. A target area within the patient may therefore be irradiated from different directions. Before irradiation the treatment is typically planned on a computer using algorithms that can simulate the radiation beams and allow the medical personnel to design the treatment beam positions and field modifiers that may be placed within the treatment beams.

Inherent in any activity carried out, by human beings in particular, is the possibility of errors. These errors may involve a misunderstanding between the physician prescribing the radiation dose and the technician who generally operate, the treatment planning system to develop a plan. Individuals might make mistakes in the generation of the plan, such as setting the wrong distance for a field as one example. The development of the treatment plan might be a complex process involving devices placed in the beam to modify the radiation field 34 in FIG. 1 produced by a linear accelerator 22. The radiation field emerges from a point source at 20. The beam modifiers such as the group represented by 32 in FIG. 1, may include shielding blocks 28, wedges 26, compensating filters 30, and dynamic intensity modulation with multi-leaf collimators represented at 24, to name a few common such devices. Compensating filters 30 are typically individually designed and manufactured for the particular field 34 for a particular patient 42. Multiple fields 34 are typically employed to converge upon a single contiguous treatment volume.

Any error in the weighting of these fields, or in the modifying devices 32 placed in the fields 34, will lead to an error in the final dose the patient receives. We also must consider the nature of the radiation itself. Ionizing radiation cannot be seen, heard, felt, tasted, or smelled and so there is no sensual feedback to the operator of the treatment planning 46 and delivery equipment 22. Radiation can only be measured with complex equipment by measuring the effects of the radiation, namely the ionization produced in air and other effects. Further, the delivery of the treatment requires that the correct devices be placed in the beam in the intended correct position and that their effects are properly accounted for by the treatment planning system 46. This lengthy and complex process has multiple opportunities for errors to be committed by persons or machines.

Most methods currently employed for preventing mistakes involve a review of the plan, the treatment beam setup, and the patient's position. However detailed information about the dose actually delivered to the patient is hard to come by, as it is difficult to make measurements within the patient's body. The standard procedures for quality control generally call for the checking of each component of the treatment planning and delivery process. It is assumed, and hoped, that when all the components are correct that the end result is correct. Yet without a feedback mechanism for the entire treatment planning and delivery process, failure to detect a problem with any component or underlying concept wilt most likely go unnoticed.

The only feedback mechanisms commonly employed consist of making a surface measurement on the patient's skin. This surface measurement can be related to a predicted dose value. However, the measurement at one or a few points does not demonstrate how the effects of all the treatment beams are adding up, nor show the dose to the target volume or critical structures. Errors can still exist at other positions within the radiation field that will not be detected, such as performing the point measurement on the central ray but the wedge 26 was reversed in position. Making measurements inside the patient is generally limited to a few points if there is a cavity available and is an invasive procedure.

Prior art includes a method for verifying the dose delivered to the patient by measuring each beam after it transverses the patient's body. Each measured ray is then back traced through the patient's body to predict the intensity of the beam before entering the patient's body. The beam intensity before entering the body is used with conventional calculation methods to compute the dose that the patient receives. However, the measured intensity of each exit ray cannot be used directly as radiation will also reach the same detector that has scattered from within the patient's body and this scatter dose contributes to the measured signal. This scatter dose can be significant and therefore needs to be subtracted from the measured exit dose prior to back tracing through the patient, but knowledge of the beam beforehand is needed to compute the amount of scattered dose. But it is this same knowledge which was to be derived from the exit dose. So the radiation beam needs to be known in order to subtract the scatter component in order to know the radiation beam. Such problems are difficult although not impossible to solve. Further, the computation of the scatter component in itself, given a known beam, is a difficult problem. These difficulties combined with the back ray tracing through the patient are very likely to result in large uncertainties in the final result that will greatly reduce the reliability and therefore usefulness of the final result for verification purposes. Systems which intend to compute the dose distribution from measured exit dose have yet to demonstrate an accuracy to be of sufficient use.

Object and Advantages

In this invention an advantage is obtained by measuring each beam prior to its entering the patient rather than to attempt to derive if from an exit measurement after the beam has transversed the patient. In our invented process such a measurement can be achieved directly with present methods and therefore be accomplished more accurately, as uncertainties introduced by scatter and attenuation in the patient, if measuring exit dose, are not introduced. The measured beam intensity is then used with conventional and known computational methods to compute the dose to the patient achieving an accuracy near that of the original treatment plan.

BRIEF SUMMARY OF THE INVENTION

The invention consists of a process for verifying the accuracy of the radiation dose delivered to patients undergoing external beam radiation therapy for the treatment of neoplastic disease. The process in reference to FIG. 1 consists of measuring and calibrating an image 40 of each radiation field 34 that is to be applied to the patient 42 in FIG. 2. The measured field images 40 are then used to recompute the dose distribution 58 in FIG. 3 to the patient 42 using anatomical cross sectional images of the patients body 42 and a dose algorithm 54. The resultant dose distributions 58 are then available for comparison to the intended prescribed treatment plan 46.

DESCRIPTION OF THE DRAWINGS

Three figures are included to facilitate understanding of the process.

Figure 1:
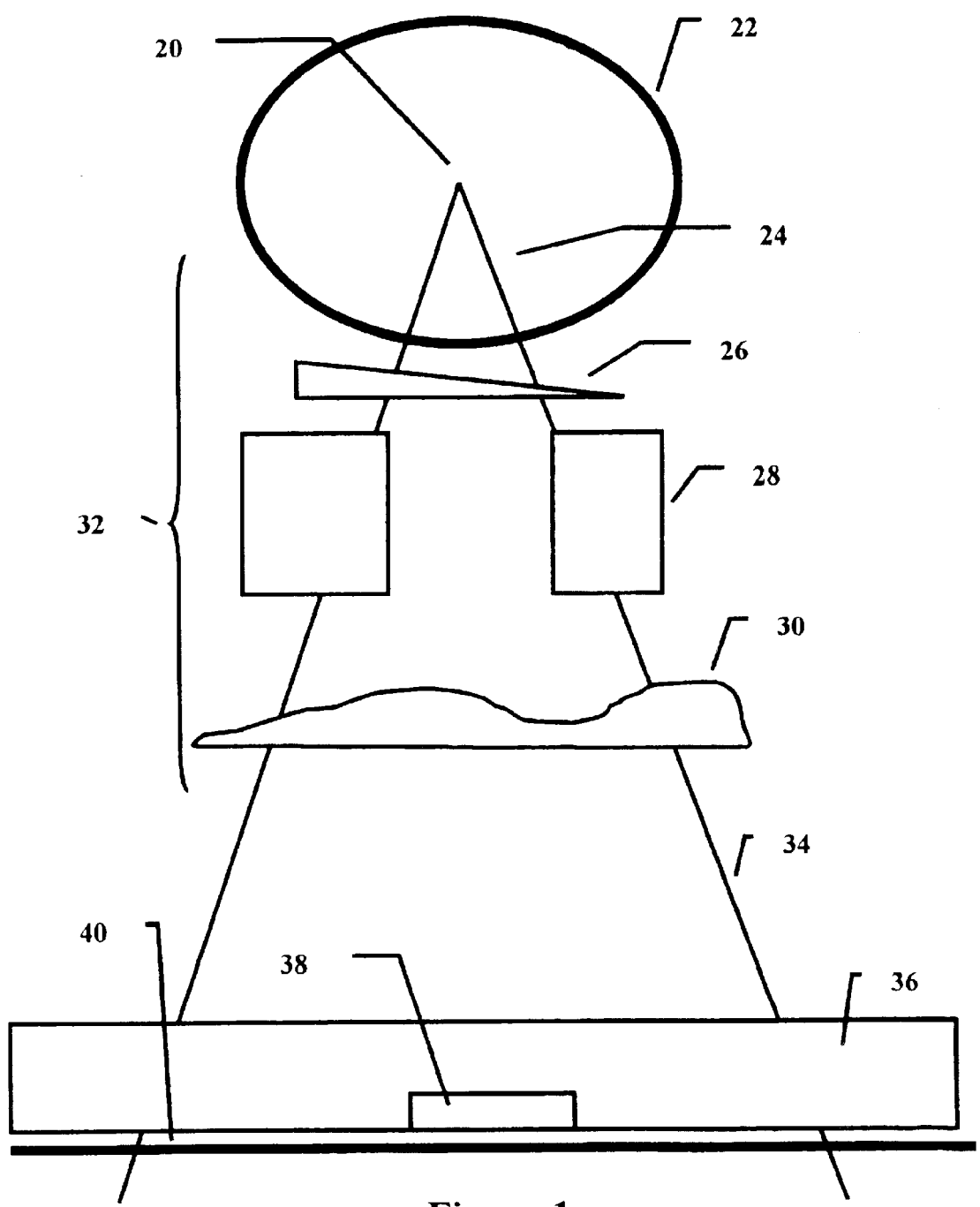
FIG. 1 shows a representation of how each treatment beam is to be imaged down stream from all the beam modifiers. The actual geometry and placement of beam modifiers will vary with the particular situation. The radiation detector 40 may be attached to the collimator of the medical accelerator or might simply be placed upon the treatment couch in the absence of the patient.

DRAWING REFERENCE NUMERALS 20 the source of radiation that creates the treatment beam.
22 the medical linear accelerator that constitutes the entire machine used to treat patients.
24 a representation of the relative placement of the field defining jaws and multi-leaf collimator should the accelerator have one.
26 the wedge which is often used in a treatment beam.
28 additional blocking typically employed.
30 compensating filters which might be used in the beam to modify the intensity distribution of the beam to obtain some desired purpose.
32 represents all of the above beam modifiers and any additional devices which might be employed with the medical linear accelerator.
34 is the emerging treatment beam that is used to irradiate the patient.
36 is the buildup bolus material used to shield out contamination electrons from the imaging device. Other means might be employed to achieve the same result.
38 represents a radiation detector such as an ion chamber or diode which might be used to measure the dose relative to some particular point on the image plane.
40 represents the image plane where the image of the radiation field is captured and will also represent the image that is captured.
42 represents the patient and a cross section through the patient.
44 is the patient support system.
46 represents the treatment planning system employed to generate the treatment plan.
48 represents the means used to transfer the images of the treatment beams to a computer 52.
50 represents the means used to transfer information about the treatment plan to the computer 52.
52 represents the computer on which a computer program 54 designed to implement the invention is running.
54 represents the computer program used to implement the functions of the invention.
56 represents the device used to display the computed dose such as a monitor.
58 represents the display of the computed dose and may include a comparison of the dose from the treatment planning computer 46.

DETAILED DESCRIPTION

The process described below is for the purpose of verifying and testing the intended treatment plan to be applied to a patient using external beam radiation. It is assumed that a radiation therapy treatment plan has been developed employing current standard state of the art treatment planning techniques represented by 46 in FIG. 3. These techniques generally involve obtaining cross sectional images of the patient's body 42 in FIG. 2 with CT scanners or other means, and generating a treatment plan using computerized treatment planning systems provided for that purpose. CT is generally the imaging modality preferred due to its geometric accuracy and that CT pixel numbers can be converted to electron density needed by dose algorithms. MRI and mechanical means for obtaining cross sectional outlines are also sometimes employed.

This present invention consists of providing a more complete feedback mechanism whereby the dose to the patient volume can be assessed in 2d planes and 3d perspective room views. The process begins with the measurement of each of the radiation fields that are to be applied to the patient as in FIG. 1. Any suitable device 40 may be used to measure the radiation field, such as x-ray film, a field imager consisting of a phosphor screen and video camera, or diode or ion chamber arrays. We will describe the process using x-ray film in ready pack, using either Kodak therapy verification film or more preferably a slower film such as Kodak EDR2 film in ready pack, and assume for here x-ray only treatments although the technique can be employed for electron therapy. Electrons, however, do not present quite the same quality control problem as x-rays do as generally only one electron field irradiates a target volume at a fixed distance and the dose delivered is closely related to the monitor units applied.

Figure 2:
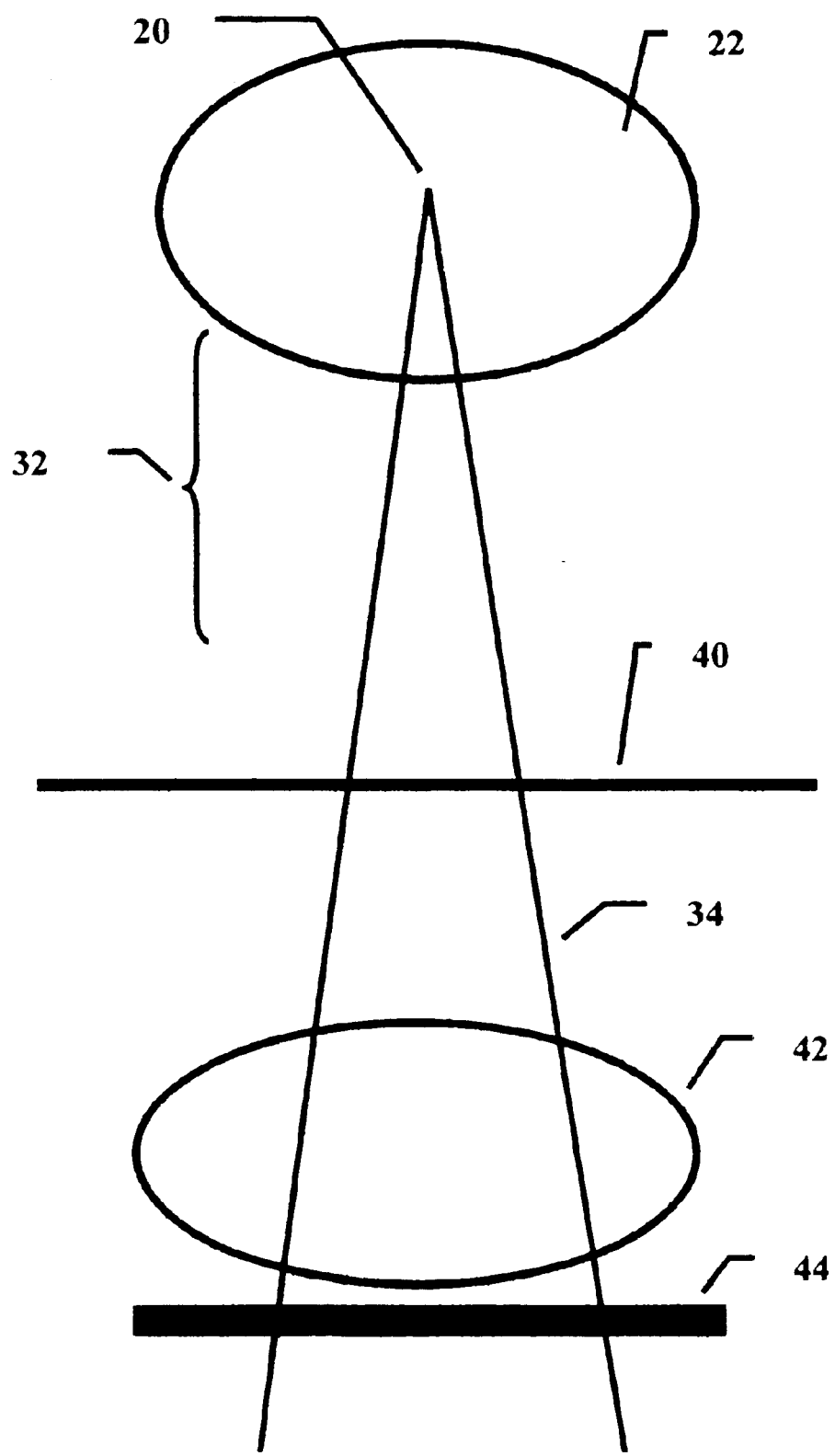
FIG. 2 depicts the relationship of the imaging device relative to the patient, should the imaging of the treatment beam be accomplished during treatment.

An image of each field is made in a plane perpendicular to the central axis of the beam, and at a known distance from the x-ray source down stream from all the in beam modifiers (as in FIG. 1). This image may be taken during a dry run without the presence of the patient, or may be taken during treatment if the patient can be treated through the imaging device (as in FIG. 2). The image is of the radiation field before it reaches the patient. There has to be sufficient buildup material (bolus) 36 above the film or device used to capture the image to shield the image receptor 40 from contamination electrons which would otherwise fog the image. For example, 1.5 cm water equivalent material is needed for 6 MeV x-rays, and 3.5 cm water equivalent material for 18 MeV x-rays. Some material in the order of 1 cm or less might be required under the imaging surface 40 to protect from back scattered contamination electrons, depending upon the equipment and surfaces employed, but a phantom with full backscatter is not to be employed under the imaging surface. Electron beams would not require buildup material. The captured field image is to approximate the in air fluence of energy emerging from the beam. The use of bolus 36 (buildup) above the image receptor 40 when using x-rays to shield out contamination electrons will not significantly degrade the measured distribution of the in air fluence. The measuring device may be placed upon the treatment couch 44 if a dry run is done without the patient, or may be attached to the collimator of the treatment machine 22 down stream from all the beam modifiers 32 as illustrated in FIGS. 1 and 2. If the shape of the beam 34 is changing while the treatment machine gantry rotates or is modulated during gantry rotation or any other movement changes the beam's position on the patient 42 while the beam is modified in shape or cross sectional intensity, then images of the field 40 must be made in sequence so that such a sequence of discrete measured beams can approximate the continuous motion employed. This can be accomplished with suitable equipment, such as a field imager with a tilt indicator for the case when only the gantry is rotating.

The response of the measuring device 40 must be corrected for and calibrated in terms of the monitor units applied on the treatment machine 22. To run a calibration curve, the calibration field size should be set (that is, the field size to which the scatter collimator factor is typically normalized and the field size at which the calibration of the treatment machine is usually specified, typically 10×10 cm, and exposures made for different monitor units covering the treatment range but possibly limited by the dynamic range of the imaging device. A software system represented by 54 provided for this application running on a computer 52 generates a curve relating monitor units as the dependent variable to the pixel value at the center of this calibration field as the independent variable. This curve is then applied to each of the measured treatment fields to convert each pixel value covering the area of the measured field to monitor units. These monitor units are referred to as relative monitor units. Allowance is made in the software system 54 provided for this application for measuring the field images 40 at different distances by applying the well known inverse square law correction. The user must know or determine the distance to the image 40 in all cases and must know the orientation of the image relative to the collimator of the treatment machine 22. If the dynamic range of the imaging device does not allow the full treatment, then either multiple images 40 are to be taken and added together, or a single image may be scaled by the ratio of the monitor units used to make the image to the monitor units intended for the field. The latter assumes that the field does not change during the delivery of the entire monitor unit prescription. The software 54 provides tools for locating the central ray of the radiation beam if at least two orthogonal edges of the field defined by the collimator are visible. Otherwise external fiducial marks must be relied upon or there must be a positive lock between the imaging device 40 and the collimator of the treatment machine 22 so that the position of the central ray is always known as well as the orientation and rotation of the field image relative to the collimator. External fiducial marks might consist of small marks whose position is known relative to the beam's central ray. With films in ready pack, one can use a pin to make marks on the film on the x and y axes of the radiation field as identified by the beam's light field that corresponds to the radiation field 34.

For an example of the meaning of relative monitor units, if the scatter collimator factor for a 40×40 cm field is 1.05 relative to 1.0 for a 10×10 cm field and a 100 monitor unit exposure is made, then the center of the 40×40 cm field has a relative monitor unit value of 1.05×100=105 relative monitor units. Off central axis in air effects (the x-ray intensity changes as a function of the distance from the central axis) will change the relative monitor unit at other positions in the image plane at 40, as will the application of beam modifying devices 32 such as shielding blocks 28, compensators 30, and wedges 26.

Another issue that must be considered is variation of the imaging device response over time, such as variation in film processing, that will change the dose response curve. We have two means of correcting for that. One is to generate a new calibration curve each time the system is used. This is expedited by providing a means to calibrate a step wedge, as typically used for this purpose, once and then using an image of the step wedge made with each set of field images. A calibration curve is generated from the image of the step wedge. A second method that is provided is to renormalized the field after conversion to relative monitor units to that at a single point measured within the field. Here a parallel plate ion chamber 38 (or cylindrical ion chamber) or a diode may be employed in the bolus stack 36 immediately above or below the imaging surface at 40. The device 38 used is also to be calibrated in terms of monitor units identically to how the imaging device 40 is calibrated. The field image 40 is then normalized at the point of measurement. This will require that the position of the measurement be known within the field image and that the measuring device not significantly affect the recorded image of the radiation field. The field images at 40 must be converted to digital form and transferred by any method 48 to the software system 54 running on a computer 52. If using film, the processed films must be digitized and converted to a format such as TIFF, PNG, or DICOM format that the application 54 is written to read.

The software system 54 developed here reads in these field images 40 in digital form and converts the pixel values to relative monitor units. The software system 54 then reads in the CT scans or other cross sectional images 42 that were used in the treatment planning process 46. The position of the isocenter of each treatment field 34 in the patient 42 is determined from the specification in the treatment plan 46. Likewise the couch, gantry, and collimator angles of the treatment machine 22 are specified. Each beam in the treatment plan 46 is then associated with the above field image 40 calibrated in terms of relative monitor units.

A dose algorithm provided in the software system 54 then computes the dose distribution to the patient in the same manner that a treatment planning system 46 does except that the input and specification for the fluence for each field 34 comes from the above measured field images 40 calibrated in terms of relative monitor units and not from a model of the beam 34 and inserted devices 32. The dose distribution 58 may then be plotted on two dimensional cross sectional images through the patient image set 42, in transverse, coronal, sagittal, or other planes, but generally in planes identical to the planes plotted with the planning system 46. The dose distribution is typically displayed on the monitor 56 of the computer employed 52. The dose result may then be directly compared to the prescription and treatment plan 46. The dose may also be displayed in perspective room views along with the anatomy and outlined regions of interest. Lastly, dose difference plots and histograms may be produced if the dose distribution from the planning system 46 is available and can be transferred in computer form 50 to the computer 52 that is running the application written for this purpose. This last step serves as a convenience to the user but is not essential to the embodiment of the invention.

The particulars of the dose algorithm employed in the software 54 are not important here as any algorithm may be employed that is capable of using a measured field fluence derived from dose to compute the dose. We are using a pencil beam algorithm that is typically employed by radiation therapy treatment planning systems 46. The pencil beam algorithm is well known in the radiation therapy journal literature. Although the field fluence is calibrated in terms of monitor units, what is actually measured at the image plane is radiation dose. Each radiation field is divided into small subunits which are commonly referred to as pencil beams. Relative monitor units are then used to normalize the weight of these small subunits of the applied field. The dose to the patient is then computed from the sum of the dose contribution from all such subunits that make up the applied radiation field and this part of the algorithm is no different from that typically employed by treatment planning systems 46. The dose computed here is according to the below two equations:

Dose a some specified point in patient=constant C times the sum of [pencil beam times relative monitor unit weight from the measured field 40 at the pencil beam's location within the field]

Where the constant C is found from solving the equation:

Dose rate cdr=Constant C times the sum of [pencil beam times the in air off axis ratio function at the pencil beam's location]

where cdr is the stated calibration dose rate for the calibration field size that the responsible physicist has defined for the particular accelerator at some specified calibration depth and distance, and the contribution the pencil beams are summed over the calibration field size. Typically the stated calibration dose rate is 1.0 centiGray per monitor unit, the calibration field size is 10×10 cm at 100 cm source surface distance, and the depth is the nominal dmax depth.

Figure 3:
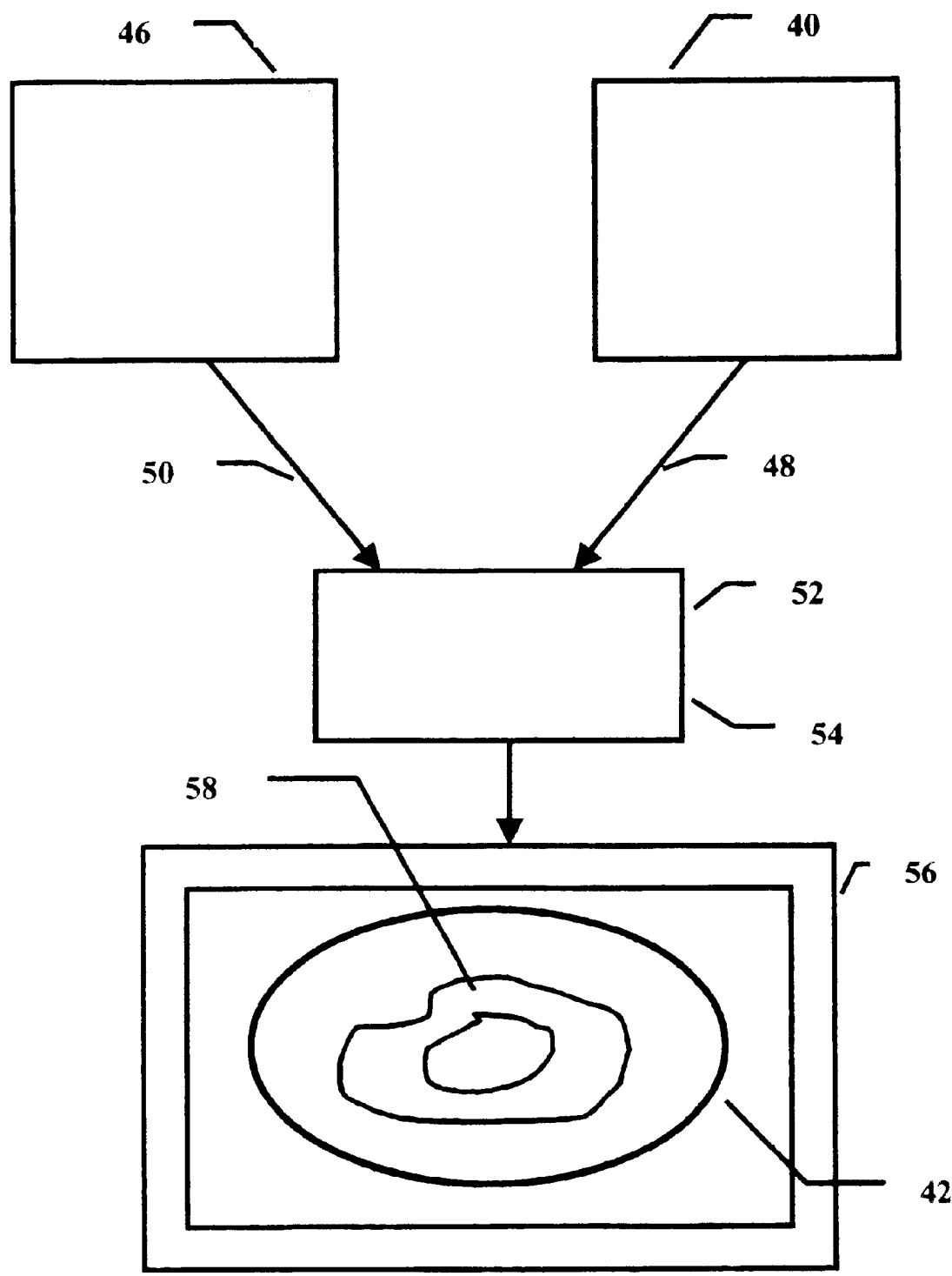
FIG. 3 depicts the flow of information. The treatment plan at 46 may be transferred through a computer network or on some medium to a computer 52 running an application 54 to support the function of this invention. This step is not essential however. The image from the imaging device 40 must be transferred through some means such as media or a computer network to the same computer 52. The application 54 computes the dose to the patient which may be displayed on the computer monitor 56 or printed to a hardcopy device such as a printer.

The result provides a dose distribution 58 computed from the measured fields 40 as depicted in FIG. 3. Any significant error in the prescribed monitor units, field size, or applied devices within the field will be evident as the dose distribution computed here will disagree with the intended plan from 46.

We have here provided a feed back mechanism for verifying the patient dose. The results may be expressed in different forms, such as dose to specific points, plotted dose distributions on a cross sectional plane through the patient, three dimensional room perspective views of the dose, standard deviation of dose difference between this result and the planning system 46.

False negatives may be possible due to common errors in both the verification system described here and the treatment planning and delivery system, but we have significantly reduced the number of common variables by starting with a measured field at 40 instead of modeling the radiation field 34 which the planning system 46 typically does. Any significant difference between the verification computed dose computed here and the plan dose should be investigated and resolved before the patient is treated. The opportunity therefore exists to resolve any false positive result that might occur.

It will be equally important for the user to understand the parameters that are not verified with this system. The system might not be very sensitive to selecting the wrong energy for the beam. Nothing is done to verify that the treatment fields are in fact properly placed on the patient. Here we are only checking the dosimetry of the plan and the effects of the devices 32 used within the beam.

What is claimed is:

1. In a radiation therapy machine having a gantry mounted radiation source for producing a plurality of radiation beams directed toward a patient at selected gantry angles, the beams including a plurality of absorbing devices to shape and modify the intensity across the beam, the process of verifying the dose delivered to or to be delivered to the patient from a plurality of such beams consisting of the steps of:

(a) measuring the output of each such intended treatment beam over the area of the beam in a plane perpendicular to the central ray of the beam using a pre-patient detector prior to impinging upon the patient, (b) using said measured output of each beam to calculate the dose to the patient from the beam using a dose algorithm, (c) accumulating the dose to the patient from all such treatment beams to produce a dose distribution, (d) using said dose distribution to compare to the intended dose to verify the correctness of the treatment.

2. The process of claim 1 performed without the patient present.

3. The process of claim 1 performed while treating the patient.

4. In a radiation therapy machine having a gantry mounted radiation source for producing a plurality of radiation beams directed toward a patient at selected gantry angles, the beams including a plurality of absorbing devices to shape and modify the intensity across the beam, the process of verifying the dose delivered to or to be delivered to the patient from a plurality of such beams consisting of the steps of:

(a) measuring the output of each such intended treatment beam over the area of the beam in a plane perpendicular to the central ray of the beam prior to impinging upon the patient, (b) using said measured output of each beam to calculate the dose to the patient from the beam using a dose algorithm, (c) accumulating the dose to the patient from all such treatment beams to produce a dose distribution, (d) using said dose distribution to compare to the intended dose to verify the correctness of the treatment, wherein said process is performed while treating the patient.

* * * * *